United States Patent [19]

Kortright et al.

[11] Patent Number: 4,818,686

[45] Date of Patent: Apr. 4, 1989

[54] CHEMICAL BLOCKING AGENT AGAINST NON-SPECIFIC BINDING OR STAINING OF AN ANTIBODY SPECIFIC FOR TERMINAL DEOXYNUCLEOTIDYL TRANSFERASE IN BIOLOGICAL SPECIMENS DURING IMMUNOASSAY

[75] Inventors: Kenneth H. Kortright, Cooper City; Scott M. Malinconico, Pembroke Pines, both of Fla.; R. Graham Smith, Dallas, Tex.

[73] Assignee: Coulter Corporation, Hialeah, Fla.

[21] Appl. No.: 907,003

[22] Filed: Sep. 15, 1986

[51] Int. Cl.$^4$ .................. G01N 53/00; G01N 53/554
[52] U.S. Cl. ........................... 435/7; 435/810; 436/503; 436/519; 436/548; 436/825
[58] Field of Search ............ 435/7, 810; 436/503, 436/519, 548, 825

[56] References Cited

U.S. PATENT DOCUMENTS

| | | | |
|---|---|---|---|
| 3,988,115 | 10/1976 | Modabber | 436/511 |
| 4,307,189 | 12/1981 | Kit | 435/6 |
| 4,460,559 | 7/1984 | Goldenberg | 424/9 X |
| 4,515,890 | 5/1985 | Manderino et al. | 435/7 |
| 4,582,791 | 4/1986 | Khanna et al. | 436/825 X |
| 4,680,274 | 7/1987 | Sakai et al. | 435/7 X |

Primary Examiner—Robert J. Warden
Assistant Examiner—Richard Wagner
Attorney, Agent, or Firm—Myron C. Cass

[57] ABSTRACT

A chemical agent is provided for significantly preventing or blocking non-specific staining or binding of an antibody specific for Terminal deoxynucleotidyl Transferase (TdT) during immunofluorescent or immunoperoxidase assay procedures. These procedures include both immunofluorescent and immunohistochemical staining of samples followed by flow cytometric and/or microscopic analysis, respectively. The invention is practiced by selective use of casein introduced into the assay procedures at an appropriate interval prior to analysis using a labelled or tagged monoclonal antibody specific to a TdT epitope. The casein utilized successfully was obtained from a large variety of sources and includes the use of a non-fat milk product.

16 Claims, No Drawings

CHEMICAL BLOCKING AGENT AGAINST NON-SPECIFIC BINDING OR STAINING OF AN ANTIBODY SPECIFIC FOR TERMINAL DEOXYNUCLEOTIDYL TRANSFERASE IN BIOLOGICAL SPECIMENS DURING IMMUNOASSAY

BACKGROUND OF THE INVENTION

This invention concerns a novel chemical agent which significantly prevents or blocks non-specific staining or binding of an antibody specific for Terminal Deoxynucleotidyl Transferase (TdT) in biological specimens during immunofluorescent or immunoperoxidase assay procedures. More particularly, the invention employs a casein selectively introduced at an appropriate stage of the assay procedure prior to analysis using a TdT specific monoclonal antibody which has been tagged or labelled to enable either immunofluorescent or immunohistochemical staining of samples followed by flow cytometric and/or microscopic analyses, respectively.

TdT is a unique DNA polymerase associated with early T-and B Lymphocyte differentiation in humans, as well as other species. Although TdT is found in a very small percentage of normal lymphoblasts, particularly in the early development of the immune system of vertebrates, elevated levels of TdT have been used in the diagnosis of human leukemias. TdT has become a valuable enzymatic marker for lymphoblastic neoplasms, such as acute lymphoblastic leukemia (ALL), chronic granulocytic leukemia (CGL) and lymphoblastic lymphoma (LL). Consequently, research has been conducted to develop methods for measurement of the frequency of lymphocytes which are positive for TdT in both normal and leukemic mammals. U.S. Pat. No. 4,307,189 describes a method for quantitative determination of TdT using labelled deoxynucleoside triphosphates which are converted by TdT to fluorescent or radioactive polydeoxynucleotides which may be quantified as a reflection of the amount of TdT originally present in the biological sample. However, this method does not employ monoclonal antibodies to TdT.

In studies published by C. Augl et al (Fed. Proc. 42:2147 1983) (Abstract) the production of monoclonal antibodies to bovine TdT has been reported without description of detailed binding recognition of the antibodies. Immunochemical studies of TdT in a variety of mammals have demonstrated that peptides of this enzyme are immunologically related when probed with antiserum prepared to the degraded enzyme from bovine thymus as reported by F.J. Bollum (Journal of Biological Chemistry 256:8768, 1981).

In studies published by F.J. Bollum, et al. (Journal of Biological Chemistry 259: 5848, 1984), the production of monoclonal antibodies to human TdT has been described. These anti-human monoclonal antibodies were widely variable in ability to recognize epitopes or determinants on TdT in human and calf cells.

Coulter Corporation, the assignee of this patent application, has introduced into the market through its Coulter Immunology Division (CID) a TdT monoclonal antibody immunoperoxidase assay kit for research use. This assay enables investigation of lymphoblastic disorders, including acute lymphoblastic leukemia (ALL) and chronic myelogenous leukemia (CML) in blast crisis studies. The TdT monoclonal antibody supplied is conjugated to a label or tag, such as fluorescein isothiocynate (FITC), for direct immunofluorecent staining and analysis by flow cytometry or fluorescent microscopy. This conjugated TdT monoclonal antibody enables anaylsis and enumeration of TdT positive cells in normal and neoplastic hematopoietic tissue and blood.

The TdT monoclonal antibody utilized in said assay kit of CID was developed by R. Graham Smith, a co-inventor named in this patent application. This monoclonal antibody is one of several developed by R. Graham Smith which are specific to a unique antigenic determinant or epitope of TdT. These monoclonal antibodies specifically recognize TdT in a wide variety of mammalian cells, including human, mouse, rat, rabbit and bovine origin. Three particular antibodies cross-react with the same epitope on TdT, and a fourth particular monoclonal antibody reacts with a distinct epitope, as determined by competitive displacement assay. These monoclonal antibodies bind to human and calf TdT, as well as extracts of rabbit, mouse and rat thymus which contain TdT-positive cells. However, these same antibodies do not bind to murine spleen which does not contain TdT-positive cells. These and other similar studies with the CID monoclonal antibodies to TdT have shown their specificity for TdT despite the species of origin and free of non-specific binding to other antigens.

These TdT monoclonal antibodies are disclosed in the co-pending patent application of R. Graham Smith, Ser. No. 802,039, filed Nov. 26, 1985 for "Monoclonal Antibodies To A Broad Range of Mammalian Terminal Deoxynucleotidyl Transferases."

We have encountered non-specific binding or staining of the cytoplasm and nucleoplasm of TdT negative cells in human peripheral blood with CID TdT specific monoclonal antibodies as well as with other commercially available TdT monoclonal antibodies. In order to develop clinically relevant analyses and enumerations of TdT positive cells in a peripheral blood sample, the nature of this non-specific binding phenomenon was sought. The assay protocol for staining for the presence of TdT was analyzed as a part of this process. The assay procedure includes the fixing of the cells being assayed in order to enable the conjugated TdT monoclonal antibody to penetrate the cytoplasm of the cell for staining the cell's nucleus for TdT.

We therefore analyzed all known fixatives that could be used for opening up large holes in the cell membrane for antibodies against TdT to enter without destroying the TdT molecule in the cell nucleus sought to be detected. A literature review revealed that other workers in the field experienced the same non-specific binding phenomenon using a two step or indirect prodecure. The nature of this binding was entirely independent of fixatives as well as the specificity of the antibodies employed in the staining process. For example, in the first step, a primary unlabelled antibody developed against TdT for staining the fixed cells for the presence of TdT was employed. A second step followed which involved adding an antibody specific for the immunoglobulin class of molecules of the species used to develop antibodies to TdT. Thus, in this indirect procedure, if the primary unlabelled antibody is a rabbit antibody against TdT, then the developing reagent carrying the fluorescent dye is a goat antibody to rabbit immunoglobulin. Therefore, the rabbit antibody to TdT binds to the TdT in the nucleus of the fixed cell followed by the goat antibody to the rabbit antibody binding to it. Since the goat antibody carries the dye, we can now visualize the staining of TdT in the fixed cells by that rabbit antibody. However, the problem arose in this indirect technique, that if the goat antibody to rabbit immunoglobulin was applied to TdT negative or positive cells, all cells stained positively. Note, that the specificity has little or no relationship to cells staining with goat anti-rabbit immunoglobulin since it is human cells being stained and no circulating rabbit antibodies could be expected to be found in the human cells. Furthermore, no circulating rabbit antibodies could be expected to be found in the human patient samples being analyzed.

An incomplete but major aid in alleviating the non-specific binding of the dye carrying goat antibody was to flood the fixed, TdT antibody stained sample with IgG which had no known specificity therein blocking the non-specific binding of dye carrying goat-anti-rabbit antiserum.

The conclusion drawn from these observations was that in order to develop a specific assay for TdT in fixed cells using a direct staining procedure as will be described herein, a blocking agent for the non-specific binding of monoclonal antibodies specific for TdT would be required. We therefore undertook the definition of the non-specific binding mechanisms which would account for background staining in TdT analyses. It was noted that af low cytometer instrument was uanble to differentiate between cytoplasmic versus nuclear TdT staining with sufficient accuracy to provide analyses from which the proper clinical conclusions could be drawn.

We have developed a unique chemical blocking agent which substantially prevents such non-specific binding of the TdT monoclonal antibody in the cytoplasm of the cells being assayed using a conjugated or tagged TdT monoclonal antibody. The chemical blocking agent is a phosphoprotein called casein and is specifically found in milk. The casein that effectively blocks non-specific binding of anti-TdT monoclonal antibodies may be derived from a variety of sources. Furthermore, a crude non-fat milk product also has been found to be effective as a blocking agent which contains casein. Further, the blocking agent is effective in an immunoassay even where a non-conjugated monoclonal antibody is utilized.

SUMMARY OF THE INVENTION

A chemical agent is provided for significantly preventing or blocking non-specific staining or binding of a monoclonal antibody specific for TdT during an immunofluorescent or immunoperoxidose testing procedure which comprises a casein protein. The casein protein can be provided by use of a non-fat milk or as derived from numerous other casein sources, as herein identified. Purified casein, technical grade casein, alpha casein, B-casein, K-casein, sodium salt of casein, N,N di-methylated casein, dephosphorylated casein, human milk and equinecasein, goat milk casein, canine milk casein and bovine and equine milk casein were determined to be capable of blocking some or all non-specific binding of TdT-FITC staining. Enzymatic hydrolysate of casein was determined to be of lesser blocking effectiveness.

The acid hydrolysate of casein was determined to be inadequate for blocking non-specific binding or staining of TdT.

The sodium salt of casein has been selected for use as the blocking agent in a TdT immunoassay kit. This blocking agent embodying the invention was determined to inhibit or block at least 90% of non-specific binding of a TdT monoclonal antibody in practicing the invention. The salt form dissolves most expediently and in the desired pH range. Thus, most effective binding or staining of the monoclonal antibody to TdT is realized in the assay procedure.

DESCRIPTION OF PREFERRED EMBODIMENTS

It is known to employ non-fat dried evaporated, powdered or non-fat milk for blocking the non-specific uptake or binding of proteins on physical filters. However, insofar as the herein inventors are aware, casein has not been utilized to block the non-specific binding of a monoclonal antibody, conjugated or non-conjugated, in an assay procedure or in an immunofluorescent assay.

The initial practice of the invention involved the conjugation of fluorescein isothyiocyanate (FITC) to the TdT monoclonal antibodies disclosed in said patent application, Ser. No. 802,039 and identified as TdT1 and TdT4. An evaporated bovine milk product was used after the conventional cell preparation procedure was completed. The suspended mononuclear cells to be assayed were treated with evaporated bovine milk in accordance with procedural steps which will be elaborated upon, washed and then analyzed in a flow cytometer EPICS ® instrument of Coulter Corporation. Marked reduction in non-specific binding of the TdT-FITC antibody in the cytoplasm was clearly discerned as compared with assays previously conducted without employing such a blocking agent.

Upon realizing such appreciable inhibition of non-specific binding of anti-TdT monoclonal antibody, it was determined that the active ingredient in this phenomenon was casein, a phosphoprotein. Casein was isolated as well as obtained from numerous sources and tested so as to qualify the blocking agent's characteristics.

Repeated tests were performed according to the procedure which follows:

1. A 100 μL (microliter) of whole blood was placed in a test tube of suitable capacity, diluted with 1 milliliter (ml) of phosphate buffered saline (PSB) and mixed;

2. 50 μL of a 1 in 10 dilution of a lysing reagent called LYSE II ® in PBS was added and mixed. LYSE II ® is the trademark of CID, Hialeah, Florida for this reagent product;

3. After a lapse of 10 seconds, 100 μL of a fixative, such as 47+% formaldehyde was added;

4. The tube's mixture then was washed three times with 4.5 mls of the PBS and centrifuged for approximately three minutes at 400 times gravity.

5. The blocking agent of the invention under test in the amount of 50 μL and 200 μL anti-TdT-FITC conjugated monoclonal antibody solution were added and incubated for approximately five minutes;

6. Washing then followed with 4.5 mls of PBS and centrifuging for 1 minute at 400 times gravity followed:

7. Resuspension in 1.0 ml of a 1 in 10 dilution of fixative in PBS was performed and analysis on an EPICS ® flow cytometer was performed.

The casein products tested in this procedure were purified casein, technical grade casein, ζ-casein, B-casein, K-casein, sodium salt of casein, N, N dimethylated casein, dephosphorylated casein, human, goat, canine and bovine or equine milk casein were tested and determined to block a substantial amount or all of the non-specific staining or binding of fTdT-FITC. Enzymatic hydrolysates of casein was determined to be only partially effective as a blocking agent. Also test was an acid hydrolysate of casein which was determined to be inadequate for blocking such non-specific staining.

Also tested were human milk, goat milk, dog milk and non-fat dry bovine milk each mixed in PBS and these were determined to be capable of blocking non-specific background binding of the TdT monoclonal antibody.

We determined that the sodium salt of casein was a most efficient chemical blocking agent, inhibiting or blocking at least 90% of non-specific binding of a TdT monoclonal antibody. The formulation used comprised 8 mg per ml of sodium salt of casein mixed in PBS to a closely approximated neutral pH. The PBS formulation comprised 0.01 Molar potassium phosphate and 0.15 Molar sodium chloride. A bacteriostatic agent such as sodium azide was used, but such an agent is not required. Although PBS was used, its function was not required.

As stated herein, a kit product employing TdT monoclonal antibody conjugated to fluorescein isothyocyanate (FITC) without the blocking agent for the immunoihistochemical staining of tissues with fluorescense or peroxidase embodying the invention has been commercially available from Coulter Corporation. The techniques for preparing the TdT conjugated are independent of the invention herein. Likewise, the fixation, staining and washing procedures for preparing the sample for flow cytometric analysis are procedures already practiced in the art, except where the chemical blocking agent is not introduced in the staining procedure for flow cytometric analysis.

The recommended staining procedure for prepared fixed mononuclear cell samples is as follows:

1. The fixed cell sample is suspended in the blocking agent preparation in the ratio of 50 μL of blocking agent per $10^6$ cells;
2. Allow to hydrate in the blocking agent for 30 minutes at room temperature which is effective to reduce non-specific binding of TdT monoclonal antibody;
3. Add $10^6$ fixed cells per 12 x 75 millimeter siliconized test tubes:
4. Prepare 200 μL of phosphate buffered albumin (PBA) containing 1X dilution of TdT-FITC per test and mix well;
5. Add 200 μL of mixture to each test and mix;
6. Incubate covered for one hour at room temperature on a shaker plate.

A washing procedure which is known from the aforementioned TdT monoclonal antibody kit product is then recommended; the analysis of the sample by flow cytometer instrumentation is then performed. This analysis procedure is conventional.

For microscopic fluorescent immunoassay, the mononuclear cells at a dilution of $2.5 \times 10^5$ cells per 0.5 ml of PBS is centrifuged (Cytospin) at approximately 140 times gravity. The slides smeared are air dried for thirty minutes and then fixed in methanol for fifteen minutes. The slides then are air dried for fifteen minutes and washed in PBS for three minutes. The slides then are subjected to an incubation period of fifteen minutes with applicant's blocking agent. Excess blocking agent is tapped off and flooding with TdT primary at ½times dilution for forty five minutes is performed. A wash with PBS for 10 minutes is followed with mounting in an aqueous mounting medium. Analysis then follows in a conventional manner.

It should be appreciated that flow cytometric and microscopic fluorescent immunoassay procedures may vary as dictated by the apparatus utilized. The specifications provided herein related to procedures practiced with products of Coulter Corporation identified. These procedures may vary as dictated by apparatus originating from sources other than Coulter Corporation. However, the advantages derived from use of applicant's chemical blocking agent comprising a casein protein will still be achieved in a fluorescent immunoassay of this direct staining type.

It is believed that this invention has been described in sufficient detail to enable the skilled artisan to understand and practice the same. Minor variations in the formulation of the blocking agent may occur to the skilled artisan without departing from the scope of the invention as set forth in the appended claims. Further, in using the conjugated form of the monoclonal antibody, a suitable detector such as dye, enzyme or other detector group molecule can be employed. The invention also is effective where a non-conjuncated monoclonal antibody is employed in the assay.

We claim:

1. In an immunoassay for Terminal Deoxynucleotidyl Transferase enzyme (TdT) in a prepared sample of mammalian cells by detecting and analyzing the specific binding of a labelled monoclonal antibody to TdT in the cytoplasm of the cells, wherein the improvement comprises introducing a casein protein substantially concurrently with introduction of the antibody to the sample to prevent non-specific binding of the labelled monoclonal antibody in the cytoplasm of the cells whereby the bound cells can be analyzed and enumerated by detection of labelled monoclonal antibody bound thereto.

2. In the immunoassay described in claim 1 in which the monoclonal antibody is conjugated to a detectable label selected from the group consisting of a dye, enzyme and other label which can signal the determinative binding of the labelled monoclonal antibody to TdT in cells of the sample.

3. In the immunoassay described in claims 1 or 2 in which said casein protein comprises a sodium salt of casein.

4. In the immunoassay described in claims 1 or 2 in which said casein protein comprises a sodium salt of casein mixed in phosphate buffered saline (PBS) to closely proximate neutral pH.

5. In the immunoassay described in claims 1 or 2 in which said casein protein is introduced into the assay prior to the determinative binding of the assay.

6. In the immunoassay described in claims 1 or 2 in which said casein protein is derived from milk.

7. In the immunoassay described in claims 1 or 2 in which said casein protein is selected from a source of milk consisting of a non-fat human, goat, canine, equine and bovine milk.

8. In the immunoassay described in claims 1 or 2 in which said casein protein is selected from the group consisting of purified casein, technical grade casein, alpha casein, B-casein, K-casein, N,N di-methylated casein, dephosphorylated and an enzymatic hydrolysate of casein.

9. An immunoassay kit for determining TdT enzyme in the nuclei of biological cells comprising a monoclonal antibody specific to TdT enzyme, a fixative for the cells, and a chemical agent for blocking non-specific binding or staining of the monoclonal antibody in the cytoplasm of the cells comprising a casein protein.

10. The immunoassay kit described in claim 9 in which said monoclonal antibody is conjugated to a detector marker.

11. The immunoassay kit described in claim 10 in which said detector marker comprises a dye.

12. The immunoassay kit described in claim 10 in which said detector marker comprises an enzyme.

13. The immunoassay kit described in claims 9 or 10 in which said casein protein is derived from milk.

14. The immunoassay kit described in claims 9 or 10 in which said casein protein comprises a sodium salt of casein.

15. The immunoassay kit described in claims 9 or 10 in which said casein protein is derived from milk selected from the group consisting of low-fat human, goat, canine, equine and bovine milk.

16. The immunoassay kit described in claims 9 or 10 in which said casein protein is selected from the group consisting of purified casein, technical trade casein, alpha casein, B-casein, K-casein, N,N di-methylated casein, dephosphorylated casein and enzymatic hydrolysate casein.

* * * * *